United States Patent
Aalders et al.

(10) Patent No.: US 10,568,996 B2
(45) Date of Patent: Feb. 25, 2020

(54) BREAST PUMP

(71) Applicant: KONINKLIJKE PHILIPS N.V., Eindhoven (NL)

(72) Inventors: Arnold Aalders, Eindhoven (NL); Marloes Josephia Maria De Wit, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 213 days.

(21) Appl. No.: 15/315,480

(22) PCT Filed: May 13, 2015

(86) PCT No.: PCT/EP2015/060675
§ 371 (c)(1),
(2) Date: Dec. 1, 2016

(87) PCT Pub. No.: WO2015/185342
PCT Pub. Date: Dec. 10, 2015

(65) Prior Publication Data
US 2017/0182231 A1    Jun. 29, 2017

(30) Foreign Application Priority Data
Jun. 5, 2014 (EP) .................................. 14171340

(51) Int. Cl.
*A61M 1/06* (2006.01)
*A61M 1/00* (2006.01)

(52) U.S. Cl.
CPC ............ *A61M 1/06* (2013.01); *A61M 1/0031* (2013.01); *A61M 1/062* (2014.02); *A61M 2205/50* (2013.01)

(58) Field of Classification Search
CPC ...... A61M 1/06; A61M 1/062; A61M 1/0031; A61M 2205/50; A61M 1/066; A61M 1/068; A61M 1/064; A61J 2205/60
See application file for complete search history.

(56) References Cited

U.S. PATENT DOCUMENTS 7,201,735 B2    4/2007  Atkin
8,057,425 B1    11/2011  Myers
(Continued)

FOREIGN PATENT DOCUMENTS

EP    1163915 A2    12/2001
EP    2687246 A1    1/2014
(Continued)

*Primary Examiner* — Bhisma Mehta
*Assistant Examiner* — Hamza A Darb

(57) ABSTRACT

The present invention relates to a breast pump (10) for extracting milk (30) from a human breast, comprising:
a first breast receiving funnel (16) for receiving a first breast (28) of a user;
a vacuum pump (20) for generating an underpressure within the first breast receiving funnel (16); and
a control unit (22) for controlling the vacuum pump (20); wherein the control unit (22) is configured to operate the vacuum pump (20) in at least two different modes, an attachment mode (48) and a milk extraction mode (50); wherein in the attachment mode (48) the control unit (22) is configured to control the vacuum pump (20) to generate a constant underpressure within the first breast receiving funnel (16) allowing the user to attach the first breast receiving funnel (16) to the first breast (28); and wherein in the milk extraction mode (50) the control unit (22) is configured to control the vacuum pump (20) to generate a time-variable underpressure profile within the first breast receiving funnel (16) for extracting milk (30) from the first breast (28).

15 Claims, 6 Drawing Sheets

(56) References Cited

U.S. PATENT DOCUMENTS

| | | |
|---|---|---|
| 2006/0211335 A1 | 9/2006 | Lantz |
| 2008/0009815 A1 | 1/2008 | Grabenkort |
| 2008/0127991 A1 | 6/2008 | Moreland |
| 2008/0177224 A1* | 7/2008 | Kelly .................. A61M 1/0037 604/74 |
| 2008/0255503 A1* | 10/2008 | Quackenbush ..... A61M 1/0031 604/74 |
| 2008/0275386 A1 | 11/2008 | Myers |
| 2014/0031744 A1* | 1/2014 | Chen ....................... A61M 1/06 604/74 |

FOREIGN PATENT DOCUMENTS

| | | |
|---|---|---|
| WO | 2011010255 A1 | 1/2011 |
| WO | 2014044472 A1 | 3/2014 |

* cited by examiner

BREAST PUMP

This application is the U.S. National Phase application under 35 U.S.C. § 371 of International Application No. PCT/EP2015/060675, filed on May 13, 2015, which claims the benefit of International Application No. 14171340.4 filed on Jun. 5, 2014. These applications are hereby incorporated by reference herein.

FIELD OF THE INVENTION

The present invention relates to a breast pump for extracting milk from a human breast.

BACKGROUND OF THE INVENTION

Breast pumps are well-known devices for extracting milk from a human breast. A breast pump may be used if the baby is not itself able to extract the milk, or if the mother is separated from the baby, for example, if away from the baby at work. The use of a breast pump to extract milk may also be used to stimulate lactation in women with a low milk supply.

Conventional breast pumps make use of vacuum to induce milk extraction from a nursing mother's breast. The pumping action of the device draws the milk from the teat to a collection vessel, and may be adjusted to the preferences of the lactating female.

Breast pumps may be manually operated, for example, by squeezing a handle or operation of a foot paddle. Breast pumps may also be electrically driven by a small electric motor. The present invention relates to a breast pump with an electrically driven vacuum pump.

In addition to the electrically driven vacuum pump such breast pumps usually comprise a breast receiving funnel for receiving the breast of the female. This breast receiving funnel is part of an expression kit that usually also comprises the collection vessel for collecting the extracted milk. The breast receiving funnel comprising a mouth and a throat. The mouth is open at an upper end and an inner surface of the mouth converges from the upper end towards the throat to form a hollow recess for receiving the female breast.

Many mothers have problems to correctly attach the breast receiving funnel of the expression kit correctly to their beast. During placement the mother has to correctly place the expression kit while at the same time having to turn on the vacuum pump with the other hand. This is sometimes a tedious action especially for unexperienced mothers. The nipple should be aligned as good as possible in the center of the breast receiving funnel. If the mother then turns on the vacuum pump, e.g. by pushing a button, the breast receiving funnel often gets out of place.

The above-mentioned problem becomes even more apparent if two expression kits are used at the same time, one for each breast. In this case it is even more difficult to correctly place the expression kits and operate the breast pump settings at the same time due to the fact that the mother does not have both hands available when using two expression kits and having to hold both of them. The first expression kit can obviously be placed with both hands. Nevertheless, the second expression kit is more difficult to be placed, since the mother has then only one hand available. After placing both expression kits to her breast, the mother will need to adjust the settings or switch on the vacuum pump. This action requires a quite un-ergonomical posture of the mother, since she has to hold both expression kits with one hand while turning on the vacuum pump with the other hand.

A known solution for such a twin breast pump is the usage of a special bra into which the expression kits are integrated. This has the advantage that the mother can use both hands for initiating the milk expression and also after starting the milk expression. This solution, however, has the disadvantage of being quite cost intensive (additional costs for the special bra). Furthermore, the mother has to at least partly undress herself to put the bra on. This is not very convenient for the mother.

WO 2008/127991 A1 discloses a manual or motorized breastpump that includes a mechanism to regulate pressure change within a breastshield chamber, including in some cases to a maintained minimum pressure that is less than ambient (atmosphere). The pressure regulator provides control for varying negative pressure between a minimum value and a maximum value (and values in between), or to achieve a specific actually measured negative pressure value within a breastshield.

US 2008/0177224 A1 discloses a programmable electric breast pump system including a vacuum pump pneumatically coupled to breast cups and a vacuum relief valve bypassing the vacuum pump. A controller receives command input from a vacuum level selector and a vacuum rate selector, and feedback from a pressure sensor measuring vacuum in the breast cups. In response, the controller cycles the relief valve between minimum and maximum vacuum setpoints to create a periodic vacuum pulse in the breast cups. By adjusting the vacuum min/max levels and vacuum rate, a user may change the strength of the pulse after let-down, or synchronize the frequency of the pulse with the natural refractory time of a lactating breast.

SUMMARY OF THE INVENTION

Therefore, it is an object of the present invention to provide a breast pump which substantially alleviates or overcomes the above-mentioned problems. In particular, it is an object of the present invention to provide a breast pump that may be attached to the female breast in an easier manner and allows a more convenient handling, especially in case two expression kits are used at the same time.

According to an aspect of the present invention, a breast pump for extracting milk from a human breast is provided, wherein the breast pump comprises:
  a first breast receiving funnel for receiving a first breast of a user;
  a vacuum pump for generating an underpressure within the first breast receiving funnel; and
  a control unit for controlling the vacuum pump;
  wherein the control unit is configured to operate the vacuum pump in at least two different modes, an attachment mode and a milk extraction mode;
  wherein in the attachment mode the control unit is configured to control the vacuum pump to generate a constant underpressure within the first breast receiving funnel allowing the user to attach the first breast receiving funnel to the first breast; and
  wherein in the milk extraction mode the control unit is configured to control the vacuum pump to generate a time-variable underpressure profile within the first breast receiving funnel for extracting milk from the first breast.

It shall be noted that the same principle may be achieved by having two different vacuum pumps, one for the attachment mode and one for the milk extraction mode. Thus, according to an alternative, a breast pump may be provided, comprising:

a first breast receiving funnel for receiving a first breast of a user;

a first vacuum pump for generating a constant underpressure within the first breast receiving funnel allowing the user to attach the first breast receiving funnel to the first breast in an attachment mode;

a second vacuum pump for generating a time-variable underpressure profile within the first breast receiving funnel for extracting milk from the first breast in a milk extraction mode; and a control unit for switching between the first and the second vacuum pump.

In addition to the "regular" milk extraction mode, in which a time-variable underpressure is provided within the breast receiving funnel for extracting milk, the presented breast pump may be operated in a so-called attachment mode. This attachment mode facilitates the attachment of the expression kit to the breast. In the attachment mode the vacuum pump generates a constant underpressure within the breast receiving funnel. This constant underpressure allows the female to easily attach the breast receiving funnel to her breast. The breast is slightly sucked into the breast receiving funnel by means of said constant underpressure, such that the expression kit of the breast pump will stick to the breast after attachment, even if the mother takes off her hands. It is to be noted that a relatively light underpressure is sufficient to guarantee this function. Even though it is preferred that the underpressure generated during the attachment mode is exactly constant over time, it shall be also noted that smaller deviations (e.g. deviations of 10%) from an exactly constant underpressure shall be still within the scope of the present invention. The term "constant underpressure" should thus be understood as "substantially constant underpressure".

In practice, this allows the mother to place the breast receiving funnel correctly on her breast while or after initiating the attachment mode. As soon as the breast receiving funnel is attached to the mother's breast, the mother has both hands free to operate the settings of the vacuum pump, since she does no longer have to hold the expression kit by herself. Then, the milk extraction mode may be initiated in order to extract milk from the breast. The initiation of the attachment mode and/or the milk extraction mode may either be done manually or automatically, as this will become more apparent from the following description.

Due to the above-mentioned possibility of having two different modes between which the vacuum pump is switchable, the handling of the breast pump is significantly facilitated for the mother. This improves the user comfort and enhances the compliance of the device. It shall be noted that the term "vacuum pump" shall not only denote a vacuum pump is the strict technical sense, but also a positive pressure pump that is able to generate an underpressure within the breast receiving funnel.

The possibility of the vacuum pump of being switchable between an attachment mode for generating a constant underpressure and a milk extraction mode for generating a time-variable underpressure profile may be implemented best by means of a multi-stroke pump. Such multi-stroke pumps generate vacuum by performing multiple pump strokes, in contrast to a single stroke pump, which generates a vacuum by only a single pump stroke (e.g. a single movement of the piston within the pump cylinder). Multi-stroke pumps may exemplarily be realized as rotatory-driven vacuum pumps. Even though it would be also conceivable to use a single-stroke pump for the present invention, a multi-stroke pump may generate a constant underpressure (within the attachment mode) in an easier manner and may be easier switched between a constant and time-variable underpressure (when switching from the attachment mode to the milk extraction mode).

It shall be noted that the present invention is not limited to the usage of a single expression kit with a single breast receiving funnel, but applies also to breast pumps with two breast receiving funnels provided in two separate expression kits or combined in a single expression kit. As it will be explained in the following, the principle of the present invention is even more advantageous if implemented in a breast pump with two separate breast receiving funnels.

According to an embodiment, the breast pump further comprises a second breast receiving funnel for receiving a second breast of the user, wherein the vacuum pump is fluidly connected to the first and the second breast receiving funnel, and wherein in the milk extraction mode the control unit is configured to control the vacuum pump to generate the time-variable underpressure profile within the first and the second breast receiving funnel for extracting milk from the first and the second breast.

Alternatively, the breast pump may comprise a second vacuum pump, wherein the first vacuum pump is fluidly connected to the first breast receiving funnel and the second vacuum pump is fluidly connected to the second breast receiving funnel. However, the usage of only one vacuum pump that is fluidly connected to both the first and the second breast receiving funnel is a more cost-saving solution. Apart from that, the usage of a single vacuum pump facilitates to generate the same time-variable underpressure profile within both breast receiving funnels, such that in both breast receiving funnels more or less the same conditions occur. This makes it more comfortable for the user.

According to a further embodiment, the control unit is in the attachment mode configured to control the vacuum pump to generate a constant underpressure within the first and the second breast receiving funnel.

The mother may thus place the first expression kit with the first breast receiving funnel on her first breast using both of her hands. She may then start the attachment mode, e.g. by pressing a button with one of her hands, while holding the first expression kit with her other hand. The mother may then remove her hands from the first expression kit, as it will remain on her first breast due to the constant underpressure that is created in the attachment mode. She may then pick the second expression kit with the second breast receiving funnel in order to place it on her second breast. Thereto, she may use both of her hands again. Since the vacuum pump already tries to generate a vacuum within the second breast receiving funnel, the second breast receiving funnel will immediately stick to her second breast, as soon as she arranges it on her second breast.

Alternatively, the control unit may be configured to generate the constant underpressure upon a first initiation of the attachment mode, e.g. by pressing a first button, only within the first breast receiving funnel, and to generate the constant underpressure upon a second initiation, e.g. by pressing a second button or the first button a second time, afterwards within the second breast receiving funnel as well. In this case, the mother would initiate the first part of the attachment mode (generation of the vacuum within the first breast receiving funnel) as soon as she has placed the first breast receiving funnel on her first breast; and she would initiate the second part of the attachment mode (generation of the vacuum within the second breast receiving funnel) as soon as she has placed the second breast receiving funnel on her second breast.

The latter-mentioned way of controlling the vacuum pump especially prevents an overload of the vacuum pump, since the vacuum pump does then not try to create a vacuum within the second breast receiving funnel before the second breast receiving funnel is attached to the second breast. Nevertheless, as soon as the mother has placed both expression kits on her breasts, she may remove her hands from the expression kits and then has both hands free for initiating the milk extraction mode, i.e. for changing the vacuum pump from the attachment mode to the milk extraction mode, e.g. by pressing a button.

Generally, it would be also conceivable in case of a breast pump with two expression kits to generate the constant vacuum during the attachment mode only in the first breast receiving funnel (and not in the second breast receiving funnel). In this case, the mother would have to hold only the second breast receiving funnel with one hand, while the first breast receiving funnel adheres to the first breast by means of the constant vacuum, so that she may initiate the milk extraction mode, e.g. by pressing a button, with her other hand.

According to a further embodiment, the breast pump further comprises an input interface, wherein the control unit is configured to initiate the attachment mode upon a manual activation of the input interface.

This input interface may be realized as a small button or touchpad or any other type of mechanical or electronical user interface. In a simple implementation the input interface may comprise only one button that is used for the complete control of the vacuum pump. In a more complicated implementation the input interface may comprise several buttons, wherein each button allows the user to initiate or control a different function. For example, the control unit may be configured to control the vacuum pump to generate a constant underpressure within the first breast receiving funnel upon a manual activation of a first button of the input interface, and to control the vacuum pump to generate a constant underpressure within the second breast receiving funnel upon a manual activation of a second button of the input interface. The same may be accomplished by providing only one button, i.e. pressing the button the first time initiates the generation of the underpressure within the first breast receiving funnel, and pressing the button a second time initiates the generation of the underpressure within the second breast receiving funnel. The input interface may alternatively comprise a voice control, gesture control, vibrational and/or acoustical control that allows the mother to initiate the attachment mode by means of a voice or gesture command.

According to a further embodiment, the control unit may be configured to switch from the attachment mode to the milk extraction mode upon a manual activation of the input interface.

In case the input interface comprises only one button, the pump would be switched from the attachment mode to the milk extraction mode after pressing the button, e.g. the third time. Alternatively, a third button could be provided on the input interface. In the latter-mentioned case, the user would have a first button for initiating the attachment mode in the first breast receiving funnel, a second button for initiating the attachment mode in the second breast receiving funnel, and a third button for initiating the milk extraction mode in both breast receiving funnels. The vacuum pump may thus be controlled in a very intuitive manner.

The input interface and/or the above-mentioned buttons of the input interface may either be arranged at or on a pump housing that comprises the vacuum pump and the control unit, or they may be arranged on one or both expression kits. The first alternative is the more cost-saving alternative, since arranging the input interface at the pump housing, which may be placed on a desktop, requires less wiring and is technically easier to achieve. The second alternative (arranging the input interface on one or both of the expression kits) is more convenient for the user, since it allows operating the breast pump with only a few fingers and the user does not have to get in contact with the pump housing that may be placed on the desktop locally remote from the expression kits.

In a further embodiment, the control unit is configured to automatically switch from the attachment mode to the milk extraction mode after a predetermined period of time.

In other words, the user only has to manually initiate the attachment mode, and the milk extraction mode will be initiated after a predetermined period of time after the initiation of the attachment mode. This facilitates the handling for the user even more. The afore-mentioned predetermined period of time may be selected by the mother according to her personal preferences. The input interface could, for example, allow setting said time period individually.

According to a further embodiment, the input interface comprises a vacuum pump adjuster for manually adjusting the constant underpressure in the attachment mode and/or for manually adjusting the time-variable underpressure profile in the milk extraction mode. The mother may thus adjust the pressures in both modes according to her personal preferences.

According to a further embodiment, a first pressure sensor is provided for measuring a first pressure within the first breast receiving funnel, wherein the control unit is configured to initiate the milk extraction mode if the first pressure is at a predetermined pressure threshold.

In this case the milk extraction mode is started automatically. Hence, the user does not have to press any extra button to initiate the milk extraction mode. The first pressure sensor may measure the pressure within the first breast receiving funnel, and as soon as the first pressure sensor recognizes that a sufficient underpressure is created within the first breast receiving funnel (which is an indicator that the first breast receiving funnel is correctly attached to the first breast), the control unit may switch the vacuum pump from the attachment mode to the milk extraction mode.

In case of a breast pump with two expression kits, the second breast receiving funnel may comprise a second pressure sensor for measuring a second pressure within the second breast receiving funnel, wherein the control unit is configured to initiate the milk extraction mode if each of the first and the second pressure are at a predetermined pressure threshold. In other words, the control unit may automatically switch from the attachment mode to the milk extraction mode if the pressure sensors detect that a sufficient vacuum is created in both breast receiving funnels indicating that both breast receiving funnels are correctly attached to the breasts.

According to a further embodiment, the first breast receiving funnel comprises a contact sensor for sensing a contact of the first breast receiving funnel with the breast, wherein the control unit is configured to initiate the attachment mode if the contact sensor senses a contact.

In this case, the attachment mode is initiated automatically as soon as the mother places the breast receiving funnel to her breast. The same may also be implemented in a breast pump with two expression kits. In this case, the second breast receiving funnel also comprises such a contact sensor.

The contact sensor itself may be realized in many ways, e.g. by means of a mechanical, electronical, optical or capacitive sensor. The contact sensor may also comprise a plurality of sensor elements that are distributed over the surface area of the breast receiving funnel. Such multiple sensing elements decrease the possibility that the attachment mode is unintentionally initiated due to an accidental contact with the breast receiving funnel. The sensing elements may, for example, be arranged at positions of the breast receiving funnels that are usually only contacted by a breast received in the breast receiving funnel, but not by other obstacles or the mother's hand.

According to a further embodiment, the first breast receiving funnel comprises a first pressure sensor for measuring a first pressure within the first breast receiving funnel, wherein the control unit is configured to control the vacuum pump based on a pressure signal of the first pressure sensor. The same is possible in case a second pressure sensor is arranged at the second breast receiving funnel.

In other words, this embodiment realizes a feedback loop from the pressure sensor to the control unit and the vacuum pump. In this way the vacuum pump may be self-regulated, such that unwanted, too high underpressures, which could cause discomfort for the user, may be prevented. The pressure signal of the pressure sensor may be used to control the vacuum pump in both the attachment mode as well as in the milk extraction mode.

According to a further embodiment, the vacuum pump is fluidly connected to the first breast receiving funnel by way of a direct connection without a membrane separating the vacuum pump from the first breast receiving funnel.

In contrast to known breast pumps of this type which use a hygienic membrane that separates the breast receiving funnel from the vacuum pump, the vacuum pump is in this case directly connected to the breast receiving funnel. Such hygienic membranes are usually made of a silicone membrane which acts as a hygienic shield between the vacuum pump and the breast and prevents milk from flowing into the hoses connecting the vacuum pump to the expression kits. When using such a hygienic membrane, the vacuum produced by the vacuum pump causes the membrane to move upwards thereby expanding the air in the chamber in which the breast/nipple is positioned, wherein this expansion creates the required vacuum at the breast. If the vacuum at the pump side is released, the membrane will move to its rest position again.

Even though such a mechanism (using a hygienic membrane) bears several advantages, especially hygienic advantages, a direct connection of the vacuum pump to the breast receiving funnel is preferred according to the present invention. With a direct connection of the vacuum pump to the breast receiving funnel it is easier to generate a constant underpressure in the attachment mode as well as to switch from this constant underpressure to the time-variable underpressure profile provided in the milk extraction mode.

According to an alternative embodiment, a porous membrane is arranged in the fluid pathway between the vacuum pump and the breast receiving funnel, wherein said porous membrane separates the vacuum pump from the first breast receiving funnel and is gas-permeable and liquid-impermeable.

Such a semi-permeable membrane allows creating an underpressure within the breast receiving funnel without having to move the membrane (since it is permeable to air). It is thus easier to generate a constant underpressure in the attachment mode as well as to switch from the attachment mode to the milk extraction mode. The semi-permeable membrane furthermore provides the advantage that no milk reaches the vacuum pump unintentionally, since it is impermeable to liquid.

According to a further embodiment, the control unit is configured to control the vacuum pump to gradually adapt the underpressure within the first breast receiving funnel when switching from the attachment mode to the milk extraction mode, and vice versa. This shall increase the user comfort.

The constant underpressure generated in the attachment mode preferably has a smaller absolute value than a maximum underpressure of the time-variable underpressure profile in the milk extraction mode.

The term "maximum underpressure" shall denote the largest negative pressure, i.e. the underpressure of the time-variable underpressure profile having the largest absolute value, i.e. the bottom dead center of the time-variable underpressure profile. It should be evident that a relatively light underpressure is sufficient for attaching the breast receiving funnel to the breast, while a stronger vacuum is needed for extracting milk from the breast. The underpressure during the attachment mode should not create any discomfort. The underpressure during the attachment mode should thus be chosen to be between $-1$ mbar and $-350$ mbar. Experiments of the applicant have shown that the underpressure generated in the attachment mode is preferably chosen to be between $-10$ mbar and $-180$ mbar, most preferably in the range of or at $-100$ mbar. The time-variable underpressure profile during the milk extraction mode ranges in contrast thereto preferably between atmosphere (maximum turning point, top dead center) and $-100$ mbar to $-350$ mbar (minimal turning point, bottom dead center).

BRIEF DESCRIPTION OF THE DRAWINGS

These and other aspects of the invention will be apparent from and elucidated with reference to the embodiments described hereinafter. In the following drawings

DETAILED DESCRIPTION OF EMBODIMENTS

Figure 1:
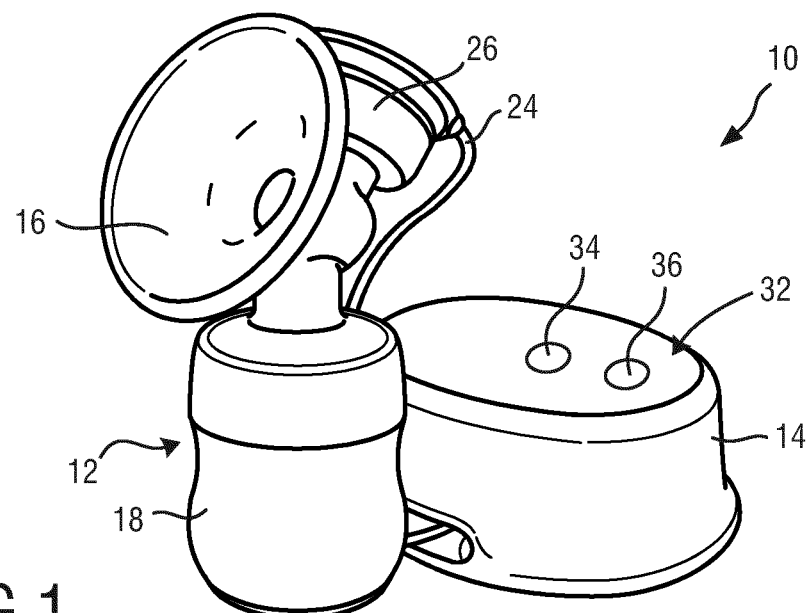
FIG. 1 shows a perspective view of a first embodiment of a breast pump.

FIG. 1 shows a first embodiment of a breast pump. The breast pump is therein denoted in its entirety with reference numeral 10.

The breast pump 10 comprises an expression kit 12 and a pump housing 14. The expression kit 12 comprises a breast receiving funnel 16 and a milk receptacle 18 in form of a baby-feeding bottle. The pump housing 14 comprises a vacuum pump 20 and a control unit 22 for controlling the vacuum pump 20 (schematically shown in FIG. 7). The vacuum pump 20 is connected to the expression kit 12 via a tube 24. The pump housing 14 may thus be arranged locally remote from the expression kit 12, e.g. on a desktop or at any other suitable position. However, this is not intended to be limiting. The pump housing 14 including the vacuum pump 20 and the control unit 22 could also be arranged at the expression kit 12. The tube 24 is connected to a vacuum chamber 26 that is comprised in the housing of the expression kit 12. The configuration of this vacuum chamber 26 will be elucidated further below with reference to FIGS. 3 and 4. The vacuum chamber 26 has the function to impart the vacuum generated by the vacuum pump 20 to the breast receiving funnel 16.

Figure 2:
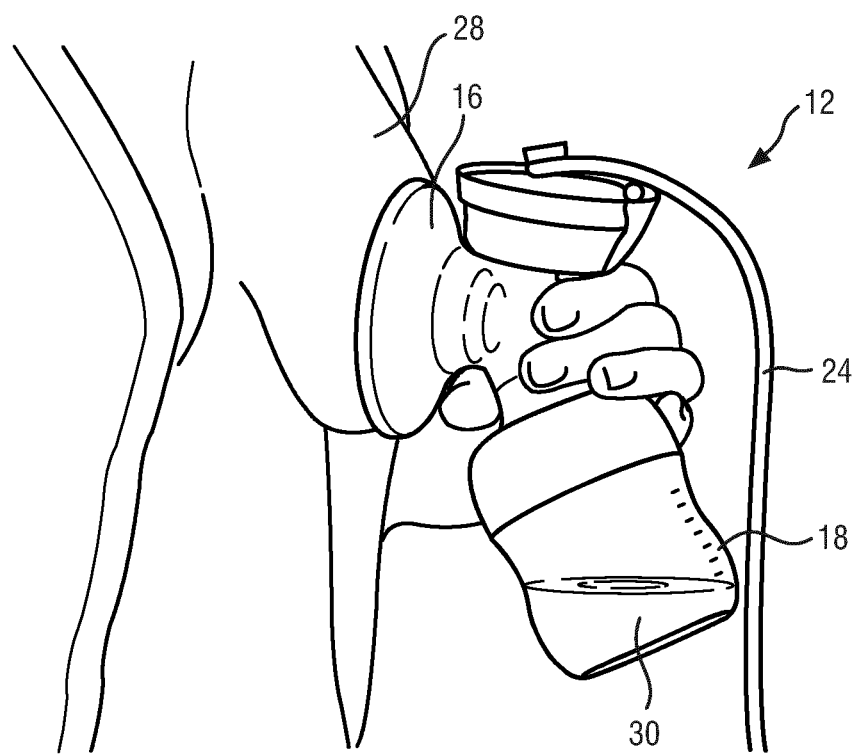
FIG. 2 shows the breast pump according to the first embodiment during application.

FIG. 2 shows the application of the breast pump 10 extracting milk from a breast 28 of a woman. The expression kit 12 is therein attached to the breast 28 by means of the breast receiving funnel 16. The center of the breast receiving funnel 16 is arranged over the nipple of the breast 28. During milk extraction the vacuum pump 20 generates an underpressure within the breast receiving funnel 16, i.e. in the space enclosed by the breast receiving funnel 16 and the breast 28. The extracted milk 30 will be collected in the milk receptacle 18.

One of the central features of the present invention is the possibility to operate the vacuum pump 20 in at least two different operation modes, an attachment mode and a milk extraction mode. The possibility to switch the vacuum pump 20 between these two different operation modes facilitates the handling for the user. In the attachment mode the control unit 22 is configured to control the vacuum pump 20 to generate a constant underpressure within the breast receiving funnel 16. This allows the user to attach the breast receiving funnel 16 to the breast 28. The mother only has to arrange the breast receiving funnel 16 at her breast 28 and then initiate the attachment mode. The constant underpressure provided in the attachment mode will cause the expression kit 12 to adhere to the breast 28, such that the mother does not have to hold the expression kit 12 any longer. This provides the advantage that the mother has her hands free for choosing the settings of the breast pump 10, in particular the settings of the vacuum pump 20, or for doing anything else. If the vacuum pump 20 is then switched to the milk extraction mode, the vacuum pump 20 will generate a time-variable underpressure profile within the breast receiving funnel 16 in order to extract milk 30 from the breast 28.

In both operation modes the vacuum pump 20 is controlled by means of the control unit 22. This control unit 22 may be realized as a processor or microchip including hardware and software stored thereon for executing the above-explained logic. The control unit 22 may be pre-programmed by the manufacturer. However, depending on the application the user may also modify the settings by means of an input interface 32.

Figure 7:
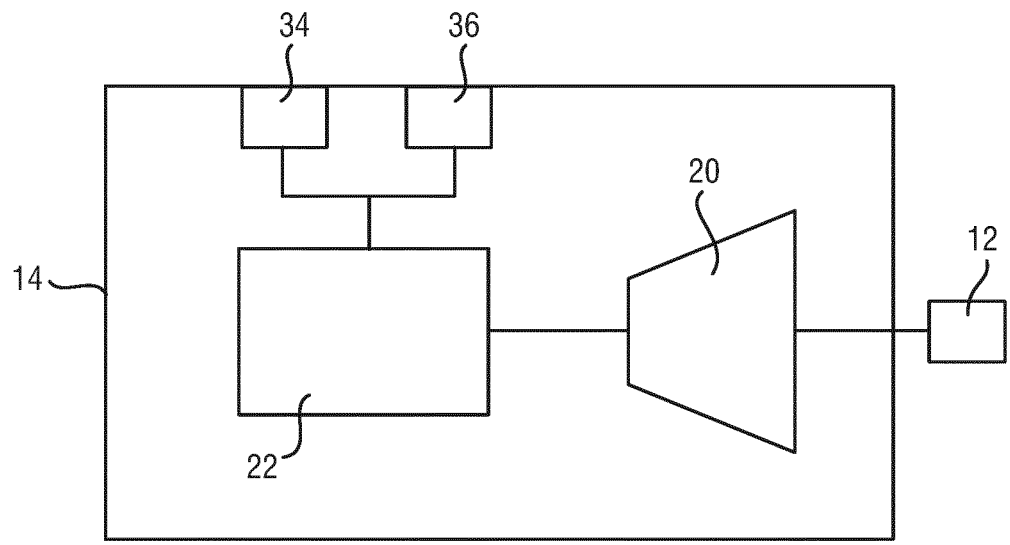
FIG. 7 shows a schematic diagram of the breast pump according to the first embodiment.

According to the first embodiment shown in FIGS. 1, 2 and 7, this input interface 32 comprises two buttons 34, 36 which are arranged at the pump housing 14. It shall be noted that the input interface may, of course, comprise more than two buttons 34, 36 or only one button. The input interface 32 may also comprise a touchscreen or any other means for electronically or mechanically changing the settings of the breast pump 10. In the presented example, buttons 34, 36 may be used to manually initiate the attachment mode and/or the milk extraction mode. The control unit 22 may, for example, be configured to initiate the attachment mode upon a manual activation of button 34, and to initiate the milk extraction mode upon a manual activation of button 36.

The mother may thus arrange the expression kit 12 at her breast 28 and then press button 34. This will initiate the attachment mode, so that a constant underpressure is created within the breast receiving funnel 16. The mother may then loose her hold on the expression kit 12. The underpressure created during the attachment mode should thus be strong enough to at least hold the extraction kit 12, as long as the milk receptacle 18 is empty. By pressing button 36 the mother may then initiate the milk extraction mode. This will cause the vacuum pump 20 to switch from the generation of a constant underpressure to the generation of a time-variable underpressure within the breast receiving funnel 16. Such time-variable underpressure profiles are well-known in the art. These time-variable underpressure profile mimic a baby's sucking action in order to provide a fast milk flow in a manner that is as comfortable as possible for the mother. Exemplary pressure profiles will be illuciated below in detail with reference to FIGS. 9 and 10.

In a further alternative, which is for simplicity reasons not explicitly shown, the input interface 32 may comprise only one button. This button could allow to initiate the attachment mode. The milk extraction mode could instead be initiated automatically a certain time (e.g. 5-20 sec) after the initiation of the attachment mode. The mother would thus have to press only one button which is even easier as the embodiment explained before with reference to FIGS. 1 and 2.

It shall be furthermore noted that the technical principle of the present invention may be also achieved by having two different vacuum pumps, one for the attachment mode and one for the milk extraction mode.

Figure 3:
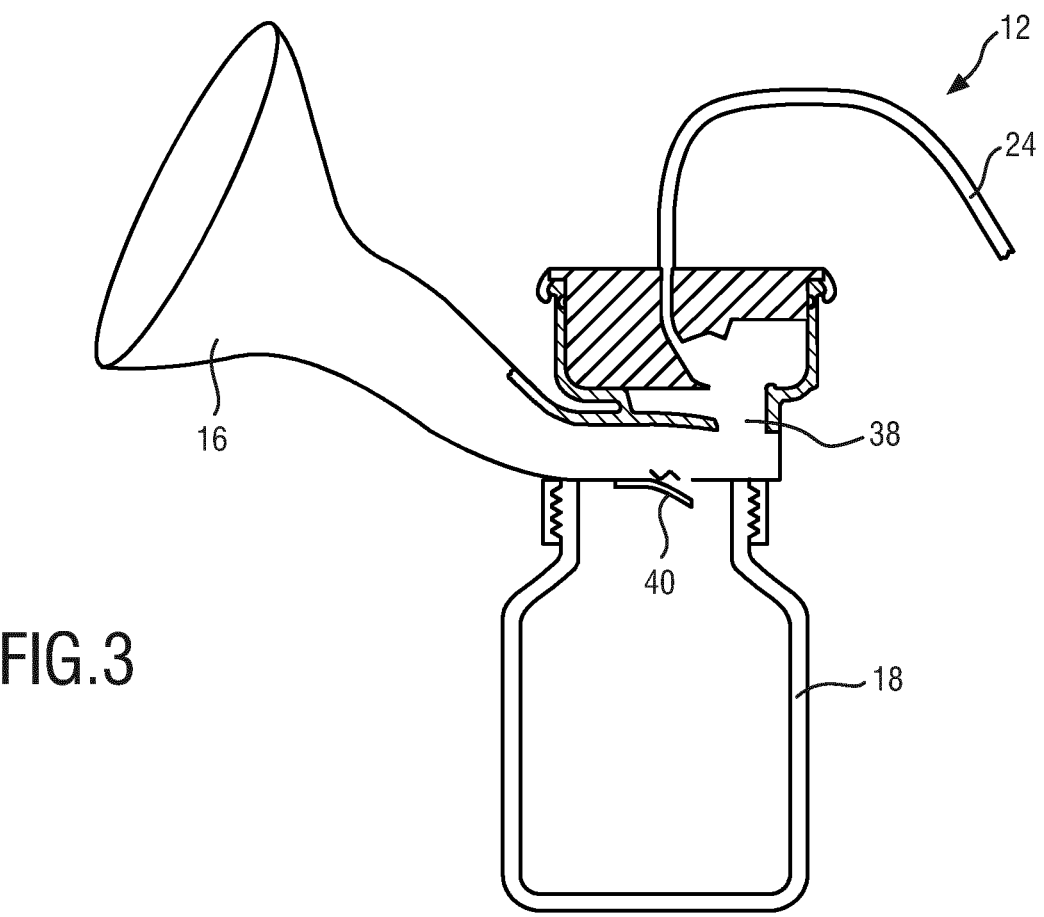
FIG. 3 shows an expression kit of the breast pump according to a first alternative.
Figure 4:
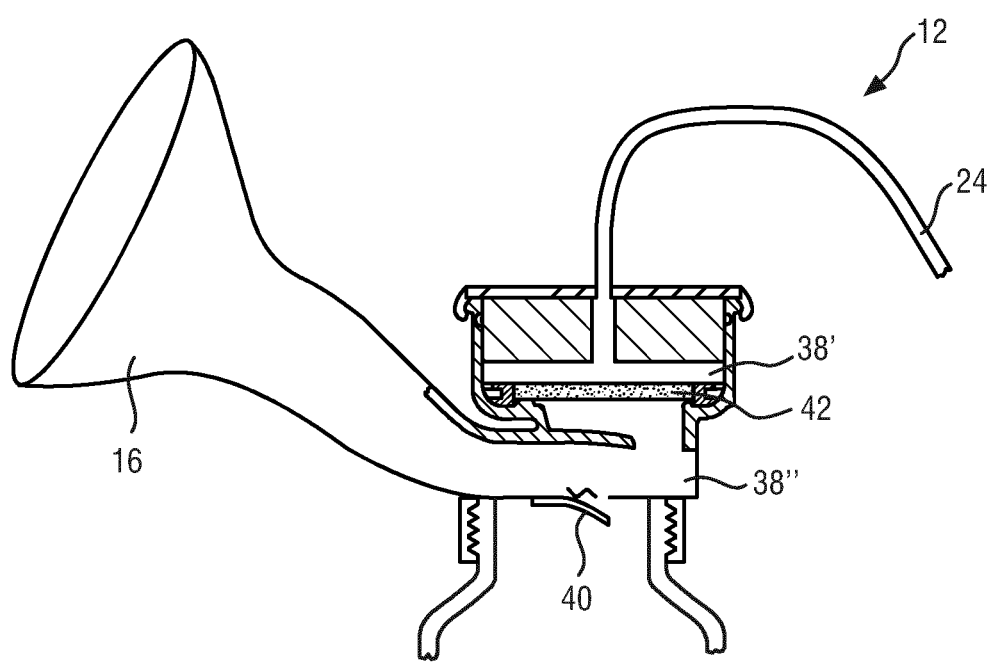
FIG. 4 shows the expression kit of the breast pump according to a second alternative.

FIGS. 3 and 4 show two different embodiments of the expression kit 12. In the embodiment shown in FIG. 3 the vacuum pump 20 is fluidly connected to the breast receiving funnel 16 in a direct manner, meaning that no membrane is provided in the pathway from the vacuum pump 20 to the breast receiving funnel 16 which separates these two parts from each other. Such a direct fluid connection provides the advantage that the constant underpressure during the attachment mode may be created in a relatively easy manner. The tube 24 in this case directly leads into a pressure chamber 38 that is formed within the interior of the housing of the expression kit 12. This pressure chamber 38 opens into the breast receiving funnel 16.

As it can be further seen from FIG. 3, the expression kit 12 further comprises a one-way valve 40. During the milk extraction mode this one-way valve 40 opens and closes automatically in accordance with the time-variable underpressure cycle generated by the vacuum pump 20. At the beginning of the underpressure cycle an underpressure will be created within the pressure chamber 38 which causes the one-way valve 40 to close and to extract the milk 30 from the breast 28. If the pressure then returns back to atmospheric pressure during said cycle, the one-way valve 40 opens up and the milk 30 flows into the milk receptacle 18 driven by gravity.

In the alternative embodiment shown in FIG. 4 the pressure chamber 38 is separated by means of a membrane 42 into a first chamber 38' and a second chamber 38". The first chamber 38' is directly connected to the vacuum pump 20 by means of the tube 24. The second chamber 38" is directly connected to the breast receiving funnel 16. The membrane 42 is preferably realized as a porous membrane which is gas-permeable and liquid-impermeable. This membrane 42 may, for example, comprise a material of polyethylene, polypropylene, polybuthylenterephthalat or polytetrafluorethylene. The membrane 42 acts as a hygienic shield that prevents milk 30 from flowing into the vacuum pump 20. It also prevents any elements present at the pump side to get into contact with the breast 28 and/or milk 30.

Since the membrane 42 is gas-permeable, it is still possible to generate a constant underpressure (in the attachment mode) as well as a time-variable underpressure profile (in the milk extraction mode). The principle for extracting milk thus remains basically the same as explained before with reference to FIG. 3. The embodiment shown in FIG. 4 furthermore provides the advantage that a smaller vacuum pump 20 may be used, since the underpressure may be generated in a more effective manner. The reason for this is that chamber 38' is much smaller than chamber 38 shown in FIG. 3. It is thus easier to generate the same underpressure with less effort.

Figure 5:
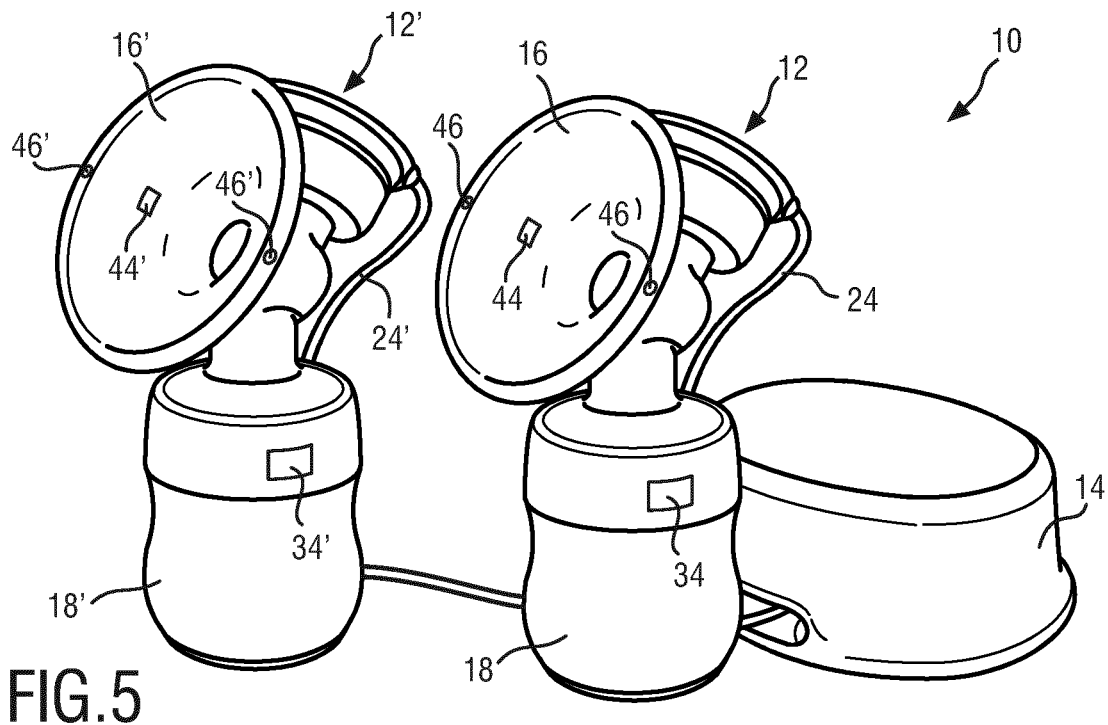
FIG. 5 shows a second embodiment of the breast pump including two expression kits.
Figure 6:
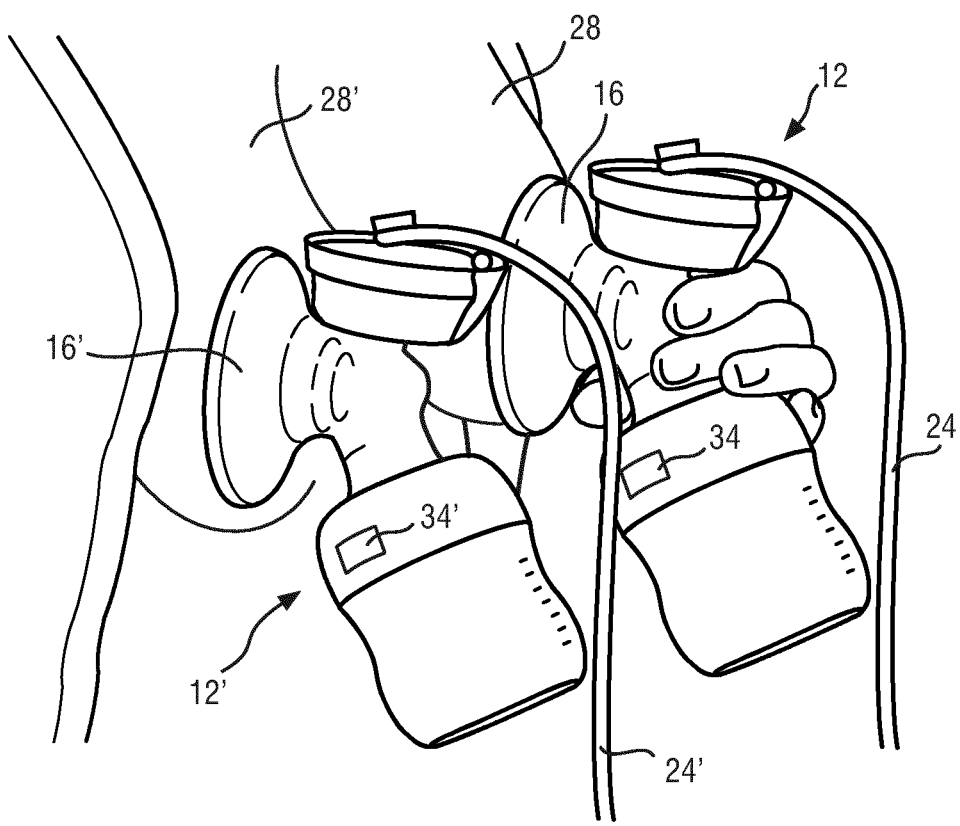
FIG. 6 shows the breast pump according to the second embodiment during application.
Figure 8:
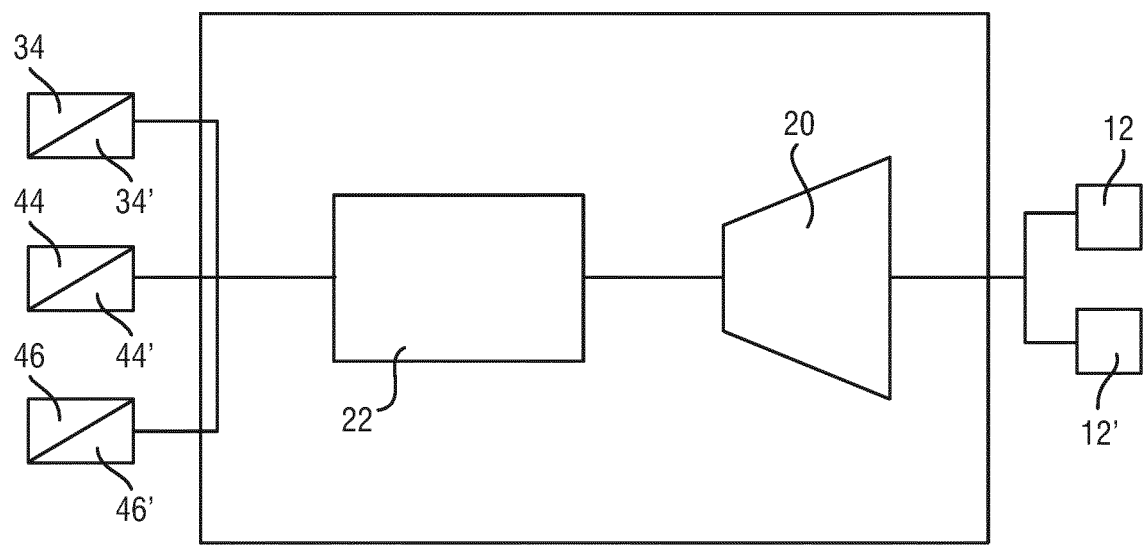
FIG. 8 shows a schematic diagram of the breast pump according to the second embodiment.

FIGS. 5 and 6 show a second embodiment of the breast pump 10 according to the present invention. FIG. 8 shows the corresponding schematic drawing. The same or similar features as shown in the first embodiment of FIGS. 1 and 2 are denoted in FIGS. 5, 6 and 8 with the same reference numerals and shall not be explained again. The basic principle of providing a breast pump 10 that may be switched between two operation modes, also remains the same. As it can be seen in FIGS. 5 and 6, the breast pump 10 according to the second embodiment, however, comprises two extraction kits 12, 12' which are both connected to the vacuum pump 20. The first expression kit 12 comprises a first breast receiving funnel 16 for receiving a first breast 28 of the user. The second expression kit 12' comprises a second breast receiving funnel 16' for receiving a second breast 28' of the user. Both expression kits 12, 12' each comprise their own milk receptacle 18, 18'.

In this case the attachment mode helps the mother even more, since she may operate the breast pump 10 in an almost hands-free manner. Similar as in the first embodiment, the attachment mode may be initiated by manually pressing the button 34, 34'. However, in this case two buttons 34, 34' may be provided. In the example shown in FIGS. 5 and 6 the buttons 34, 34' are provided at or on the expression kits 12, 12'. Compared to a provision of these buttons 34, 34' on the pump housing 14 this enables an even more ergonomic handling of the device. Pressing button 34 causes an initiation signal that in turn causes the control unit 22 to control the vacuum pump 20 to generate a constant underpressure within the first breast receiving funnel 16. Pressing button 34' causes a second initiation signal that in turn causes the control unit 22 to control the vacuum pump 20 to generate a constant underpressure within the second breast receiving funnel 16'. Using these two buttons 34, 34' the mother may thus attach both expression kits 12, 12' one after the other at her breasts 28, 28'.

An extra button 36 as shown in FIG. 1 may be provided for starting the milk extraction mode. However, in the example shown in FIGS. 5 and 6 the initiation of the milk extraction mode is solved in an even more sophisticated manner. Both breast receiving funnels 16, 16' may each comprise a pressure sensor 44, 44'. The first pressure sensor 44 is configured to measure the pressure within the first breast receiving funnel 16. The second pressure sensor 44 is configured to measure the pressure within the second breast receiving funnel 16'. These pressure sensors 44, 44' enable an automatic initiation of the milk extraction mode as soon as the control unit 22 recognizes that both expression kits 12, 12' are correctly attached to the breasts 28, 28' of the user. In other words, as soon as the pressure sensors 44, 44' detect a sufficient underpressure indicating a correct attachment, they may send an initiation signal to the control unit 22 which in turn controls the vacuum pump 20 to switch from the attachment mode to the milk extraction mode in order to extract milk from both breasts 28, 28'.

Alternatively to a manual initiation of the attachment mode, the attachment mode may also be initiated automatically. Each breast receiving funnel 16, 16' may thereto comprise one or more contact sensors 46, 46' for sensing a contact of the breast receiving funnels 16, 16' with the breasts 28, 28'. The control unit 22 may be configured to initiate the attachment mode if the one or more contact sensors 46, 46' senses a contact. Preferably, more than one such contact sensor 46, 46' is provided. The contact sensors may, for example, be distributed over different positions on the breast receiving funnels 16, 16', such that the constant underpressure is only generated if the breast receiving funnels 16, 16' are correctly arranged at the breast 28, 28'. Similar as the buttons 34, 34', the first contact sensors 46 may initiate the generation of the underpressure within the first breast receiving funnel 16, and the second contact sensors 46' may initiate the generation of the underpressure within the second breast receiving funnel 16'.

Figure 9:
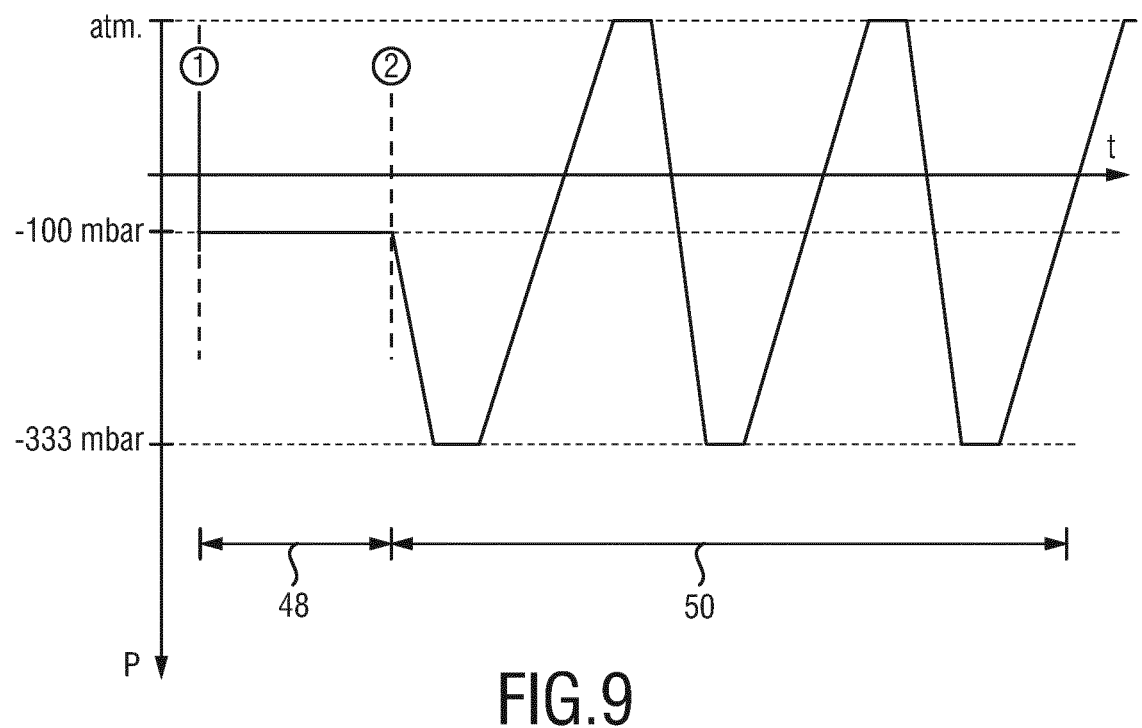
FIG. 9 shows a diagram illustrating a way of operating the vacuum pump of the breast pump according to the present invention.
Figure 10:
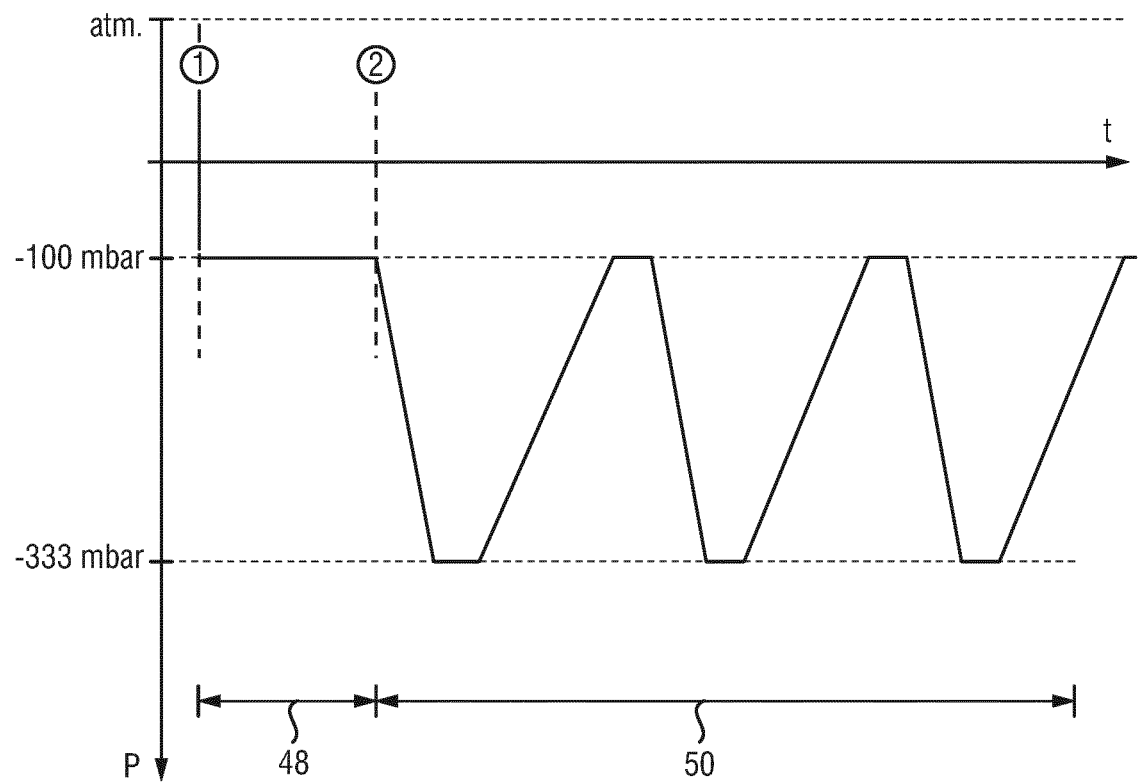
FIG. 10 shows a diagram illustrating an alternative way of operating the vacuum pump of the breast pump according to the present invention.

FIGS. 9 and 10 schematically illustrate two alternative ways of operating the vacuum pump 20 according to the principle of the present invention. Reference numeral 48 indicates the attachment mode. Reference numeral 50 indicates the milk extraction mode. At point 1 the attachment mode 48 is initiated. At point 2 the milk extraction mode 50 is initiated.

During the attachment mode 48 a constant underpressure is generated that is in the order of −100 mbar. A vacuum of around −100 mbar is estimated to be low enough to prevent pain and large enough to hold the expression kits 12, 12' on the breasts 28, 28', at least as long as the milk receptacles 18, 18' are empty. In order to keep the empty expression kits 12, 12' to the breasts 28, 28', the vacuum force should be in the order of 5 N (50 g/0.1 friction coefficient). A force of 5 N would require a surface area of around 500 mm$^2$ to generate an underpressure of −100 mbar. This is a reasonable surface area for the breast receiving funnel 16, 16'. However, it shall be noted that other surface areas, forces and pressures may be used. FIG. 9 only illustrates an example.

During the milk extraction mode 50 a time-variable pressure profile is generated, wherein the pressure within the breast receiving funnel 16, 16' may vary, for example between −300 mbar and atmospheric pressure. It is especially preferred if the minimal turning point of the pressure profile is at −333 mbar. During the pressure cycle 50 the pressure preferably drops in each cycle from atmospheric pressure within 900 msec to −333 mbar, then stays for a short time at −333 mbar and returns back to atmospheric pressure again. The pressure increase from −333 mbar to atmospheric pressure may be performed in a slower manner (e.g. within 300-400 msec) than the pressure drop from atmospheric pressure to −333 mbar.

If the pressure within the breast receiving funnel 16, 16' returns back to atmosphere in each pressure cycle, it is clear that the user (mother) has to actively hold the expression kits 12, 12' with her hands as soon as the milk extraction mode 50 is initiated. Otherwise, the expression kits 12, 12' would drop. However, it shall be noted that this is generally not a problem, since the user usually does not need to change the settings of the breast pump 10 during the milk extraction mode 50.

Nevertheless, this may be improved by modifying the pressure cycle within the milk extraction mode 50 as shown in FIG. 10. In the example shown in FIG. 10 the pressure does not return back to atmospheric pressure. The maximum turning points of the pressure profile during the milk extraction mode 50 are in this case selected to be at or around −50 mbar to −100 mbar, such that there is still a small vacuum. It shall be noted that the vacuum at the maximum turning points of the milk extraction mode 50 may even be lower than −100 mbar in order to account for the fact that the milk receptacle fills up during the milk extraction and thus gets heavier and heavier.

Figure 11:
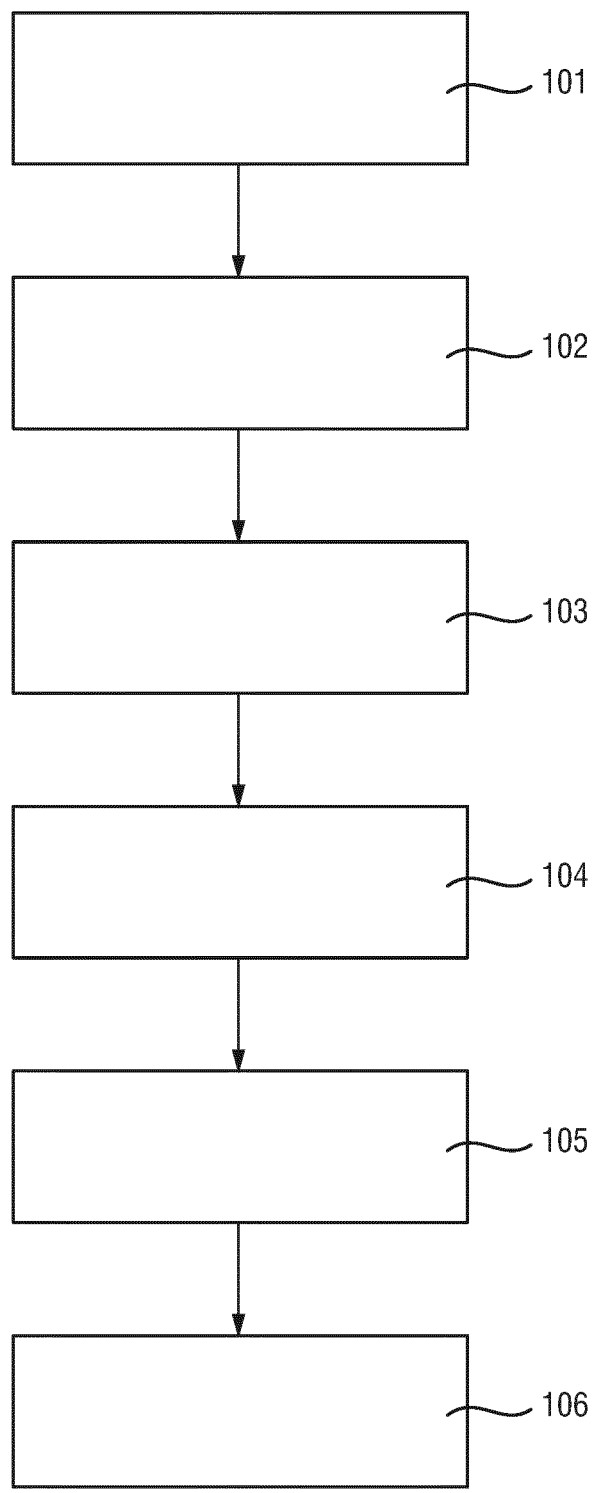
FIG. 11 schematically illustrates a way of handling the breast pump according to the present invention during application.

FIG. 11 summarizes the method according to the present invention in a schematic manner for the case of two expression kits 12, 12'. In the first step 101 the mother places the first expression kit 12 on her first breast 28. In the second step 102 she initiates the generation of the constant vacuum within the first breast receiving funnel 16. Afterwards, she may remove her hands from the first expression kit 12 (step 103), since the first expression kit 12 remains on her first breast 28 due to the applied constant underpressure within the first breast receiving funnel 16. In step 104, the mother may pick the second expression kit 12' in order to place it on her second breast 28'. In step 105, the mother may start the generation of the constant vacuum within the second breast receiving funnel 16'. After that, the milk extraction mode may be initiated in step 106. As explained before, both the attachment mode 48 and the milk extraction mode 50 may either be initiated manually or automatically.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A breast pump for extracting milk from a human breast, comprising:
a first breast receiving funnel for receiving a first breast of a user;
a vacuum pump, fluidly coupled to the first breast receiving funnel, for generating an underpressure within the first breast receiving funnel; and
a control unit for controlling the vacuum pump;
wherein the control unit is configured to control the vacuum pump to operate in at least two separate and distinct switchable modes of operation that include at least an attachment mode solely to facilitate placement and attachment of the first breast receiving funnel to the first breast and a milk extraction mode, separate and distinct from the attachment mode, for extracting milk, via the first breast receiving funnel, from the first breast;
wherein, for the attachment mode, the control unit controls the vacuum pump, in response to placing the first breast receiving funnel on the first breast, to generate within the first breast receiving funnel a constant underpressure, wherein the constant underpressure (a) enables placement of the first breast receiving funnel on the first breast and (b) guarantees that the first breast receiving funnel will stick to the first breast after placement and attachment in the attachment mode; and
wherein, for the milk extraction mode, the control unit controls the vacuum pump, in response to switching from the attachment mode to the milk extraction mode, to generate an alternating underpressure having a time-variable profile within the first breast receiving funnel to facilitate extracting milk via the first breast receiving funnel from the first breast.

2. The breast pump according to claim 1, further comprising a second breast receiving funnel for receiving a second breast of the user, wherein the vacuum pump is fluidly connected to the first and the second breast receiving funnels, and wherein in the milk extraction mode the control unit is configured to control the vacuum pump to generate the time-variable profile within the first and the second breast receiving funnels for extracting milk from the first and the second breasts.

3. The breast pump according to claim 2, wherein the control unit is further configured to control the vacuum pump in the attachment mode to generate the constant underpressure within the first and the second breast receiving funnels.

4. The breast pump according to claim 1, further comprising an input interface, wherein the control unit is configured to initiate the attachment mode upon a manual activation of the input interface.

5. The breast pump according to claim 4, wherein the control unit is configured to switch the vacuum pump from the attachment mode to the milk extraction mode upon a manual activation of the input interface.

6. The breast pump according to claim 4, further comprising a first expression kit which comprises the first breast receiving funnel and a milk receptacle connected to the first breast receiving funnel, wherein the vacuum pump and the control unit are arranged locally remote from the first expression kit, and wherein at least a part of the input interface is arranged at the first expression kit.

7. The breast pump according to claim 4, further comprising a first expression kit which comprises the first breast receiving funnel and a milk receptacle connected to the first breast receiving funnel, wherein the vacuum pump and the control unit are arranged in a pump housing locally remote from the first expression kit, and wherein at least a part of the input interface is at the pump housing.

8. The breast pump according to claim 1, wherein the control unit is configured to automatically switch the vacuum pump from the attachment mode to the milk extraction mode after a predetermined period of time.

9. The breast pump according to claim 1, further comprising a first pressure sensor for measuring a first pressure within the first breast receiving funnel, wherein the control unit is configured to initiate the milk extraction mode if the first pressure is at a predetermined pressure threshold.

10. The breast pump according to claim 1, further comprising a contact sensor for sensing a contact of the first breast receiving funnel with the first breast, wherein the control unit is configured to initiate the attachment mode if the contact sensor senses the contact of the first breast receiving funnel with the first breast.

11. The breast pump according to claim 1, wherein the first breast receiving funnel comprises a first pressure sensor for measuring a first pressure within the first breast receiving funnel, and wherein the control unit is configured to control the vacuum pump based on a pressure signal of the first pressure sensor.

12. The breast pump according to claim 1, wherein the vacuum pump is fluidly connected to the first breast receiving funnel by way of a direct connection without a membrane separating the vacuum pump from the first breast receiving funnel.

13. The breast pump according to claim 1, wherein in a fluid pathway between the vacuum pump and the first breast receiving funnel a porous membrane is arranged, wherein said porous membrane separates the vacuum pump from the first breast receiving funnel and is gas-permeable and liquid-impermeable.

14. The breast pump according to claim 1, wherein the control unit is configured to control the vacuum pump to gradually adapt the underpressure within the first breast receiving funnel when switching from the attachment mode to the milk extraction mode, and vice versa.

15. A breast pump for extracting milk from a human breast, comprising:
 a first breast receiving funnel for receiving a first breast of a user;
 a first vacuum pump fluidly coupled to the first breast receiving funnel;
 a second vacuum pump fluidly coupled to the first breast receiving funnel; and
 a control unit which is configured:
  (i) to control the first vacuum pump in an attachment mode, in response to placing the first breast receiving funnel on the first breast, to generate within the first breast receiving funnel a constant underpressure, wherein the attachment mode comprises one of at least two separate and distinct switchable modes of operation, the attachment mode being solely to facilitate placement and attachment of the first breast receiving funnel on the first breast, wherein the constant underpressure (a) enables placement of the first breast receiving funnel on the first breast and (b) guarantees that the first breast receiving funnel will stick to the first breast after placement and attachment in the attachment mode, and
  (ii) to control the second vacuum pump in a milk extraction mode, separate and distinct from the attachment mode, in response to switching from the attachment mode to the milk extraction mode, to generate an alternating underpressure having a time-variable profile within the first breast receiving funnel to facilitate extracting milk, via the first breast receiving funnel, from the first breast in the milk extraction mode.

* * * * *